(12) United States Patent
Paton

(10) Patent No.: US 6,376,245 B1
(45) Date of Patent: Apr. 23, 2002

(54) ASSOCIATIONS OF ANTAGONISTIC PROKARYOTES WITH EUKARYOTES

(75) Inventor: Alan McEwan Paton, deceased, late of Aberdeen (GB), by Isabel Helen Gourlay Paton, executor

(73) Assignee: Aberdeen University, Aberdeen (GB)

( * ) Notice: Subject to any disclaimer, the term of this patent is extended or adjusted under 35 U.S.C. 154(b) by 0 days.

(21) Appl. No.: 09/593,346

(22) Filed: Jun. 14, 2000

Related U.S. Application Data

(63) Continuation of application No. 09/338,355, filed on Jun. 22, 1999, now abandoned, which is a continuation of application No. 09/093,558, filed on Jun. 8, 1998, now abandoned, which is a continuation of application No. 08/601,012, filed as application No. PCT/GB94/01791 on Aug. 16, 1994, now abandoned.

(30) Foreign Application Priority Data

Aug. 24, 1993 (GB) ............................................. 9317588

(51) Int. Cl.$^7$ ............................ C12N 5/04; C12N 5/10; A01H 5/00
(52) U.S. Cl. ....................... 435/418; 435/419; 435/420; 435/430; 435/245; 435/259; 435/822; 800/298; 800/301; 800/317.2; 800/317.4; 424/93.7
(58) Field of Search ................................. 435/420, 430, 435/822, 245, 259, 418, 419; 424/93.7; 800/298, 301, 317.2, 317.4

(56) References Cited

U.S. PATENT DOCUMENTS 4,569,841 A 2/1986 Liu .............................. 424/93

FOREIGN PATENT DOCUMENTS

| EP | 0 472 494 A2 | 2/1992 |
| GB | 2 036 792 A | 7/1990 |
| WO | WO 85/00828 | 2/1985 |
| WO | WO 90/13224 | 11/1990 |

OTHER PUBLICATIONS

Dorland's Medical Dictionary, 27th ed., W.B. Saunders Co. Philadelphia, PA, pp. 180 and 1332, 1988.*
Finegold et al. Bailey and Scott's Diagnostic Microbiol., C.V. Mosby Co., St. Louis, MO, p. 134, 1978.*
Aloysius, S. et al., "Artificially Induced Symbiotic Associations of L–Form Bacteria and Plants", *J. Appl. Bacteriol.*, 1984, 56, 465–477.
Amijee, F. et al., "Non–pathogenic Association of L–form Bacteria (*Pseudomonas syringae* pv. Phaselocola) with Bean Plants (*Phaseolus vulgaris L.*) and its Potential for Biocontrol of Halo Blight Disease", *Biocontrol Sci. Tech.*, 1992, 2, 203–214.
Madoff, S., "Introduction to the Bacterial L–Forms", in *The Bacterial L–Forms*, Madoff (ed.), Marcel Dekker, Inc., New York, 1–20.
Paton, A.M., "L–forms: Evolution of Revolution?", *J. Appl. Bacteriol.*, 1987, 63, 365–371.
Paton, A.M. et al., "Methods for the Establishment of Intracellular Associations of L–forms with Higher Plants", *J. Appl. Bacteriol.*, 1991, 71, 59–64.
Strang, J. et al., "L–forms of *Bacillus brevis* and their Potential Use as Plant Associated Biocontrol AGents", *J. Appl. Bacteriol.*, 1989, 67,. xli–xlii.
Strang, J. et al., "Induction of *Bacillus brevis* L–forms", *J. Appl. Bacteriol.*, 1991, 70, 47–51.

* cited by examiner

*Primary Examiner*—Christopher R. Tate
(74) *Attorney, Agent, or Firm*—Kinney & Lange, P.A.

(57) ABSTRACT

The invention provides a process for protecting whole eukaryotes or parts thereof from an invasive attack from an invasive agent which comprises, selecting a prokaryotic bacterium which is capable of forming an L-form association with a host eukaryote and introducing an L-form bacteria into said host, wherein the bacteria is also selected to be antagonistic to the invasive agent. This process allows the protection of plants and plant parts against invasive organisms with which they have not already had contact.

13 Claims, 6 Drawing Sheets

(C)

(C)

(T)

(C)

ASSOCIATIONS OF ANTAGONISTIC PROKARYOTES WITH EUKARYOTES

Figure 1:
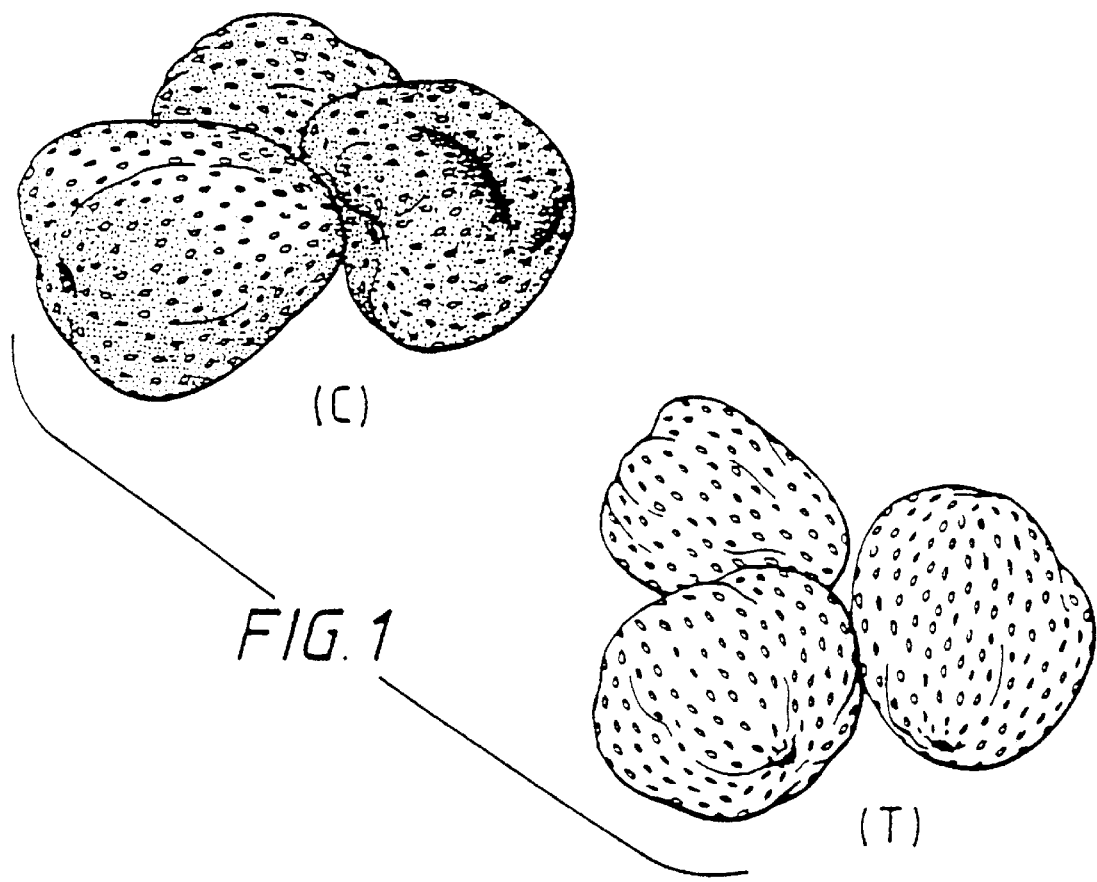

The present application is a continuation application of U.S. application Ser. No. 09/338,355 filed Jun. 22, 1999 now abandoned, which is a continuation of U.S. application Ser. No. 09/093,558, filed Jun. 8, 1998 now abandoned, which is a continuation of U.S. application Ser. No. 08/601,012, filed Jul. 16, 1996 now abandoned, which is the U.S. National Phase of PCT/GB94/01791 filed Aug. 16, 1994 claiming priority from British Application Serial No. 9317588.3, filed Aug. 24, 1993.

The present invention relates to antagonistic prokaryotic/eukaryotic associations, and particularly to the formation of associations of eukaryotic organisms with L-form bacteria antagonistic to a secondary organism with the effect of conferring the antagonism on the eukaryote.

L-form bacteria are bacteria without cell walls which can be induced by suppressing cell wall synthesis with agents such as penicillin (Madoff, 1986, Introduction to the Bacterial L-forms in "The Bacterial L-forms". Marcel Decker, New York, pp 1–20). The artificial production of intracellular associations of L-forms with plants was first described by Aloysius & Paton (1984); Artificially Induced Symbiotic Associations of L-form Bacteria and Plants. Journal of Applied Bacteriology 56, 465–477). A variety of procedures are now available to achieve such associations (Paton & Innes, 1991. Methods for the establishment of Intra-cellular Associations of L-form bacteria and higher plants. Journal of Applied Bacteriology 71, 59–64).

In our EP-0136035 there are described associations of prokaryotic organisms and eukaryotic plant cells produced by bringing their L-form into contact with the plant cell. The scientific principles underlying the practical applications of the present invention have as their starting point the said European Patent disclosure which reveals that L-form prokaryotes, produced from bacteria with entire cell walls, can be induced to enter and become viably established in eukaryotic organisms such as angiosperms.

Various methods for the preparation of L-form inocula for this purpose are available e.g. by the isolation and culture of pure L-forms (stable or unstable) or by using a heterogeneous mixture of L-forms and cell-walled bacteria formed by the introduction of an inducing agent into a fresh suspension of bacteria in a protective osmoticum. It has also been revealed that plant associations with L-form bacteria can be created using such inocula by a variety of procedures, for example, by contacting germinating seed directly with L-form containing inocula whereby the root system is infected leading to further passage of the organism within the plant or by direct invasion of the plant tissue using, for example, hypodermic inoculation techniques (Paton, (1987) Journal of Applied Bacteriology 63, 365–371).

We have now found that if the eukaryotic host and the prokaryotic bacteria are correctly chosen, it is possible to achieve not just protection of the host from subsequent attack by the walled form of the L-form bacteria, although this may occur, but also protection of the host against quite different invasive organisms to which the bacteria is antagonistic. It is thus possible in the first aspect of the invention to provide means for protecting a host plant from infection by an invasive organism unrelated to the associated prokaryote, by selecting a prokaryote which is both capable of forming an L-form association with the host eukaryote, and which is antagonistic to a selected invasive organism.

It is also possible to select an association of L-form prokaryote and eukaryotic host in which the L-form prokaryote has the effect of protecting the host plant against the entire forms of the selected L-form prokaryote, and also protecting the plant and/or fruits thereof or other commercially valuable parts of the plant against invasive agents to which the L-form prokaryote selected is antagonistic.

There is no prior art of which we are aware that reveals that plant disease can be controlled by utilising associations of L-form bacteria antagonistic to selected plant pathogens since previous disclosures indicate that the protection can be produced against walled form of a bacterial pathogen due to a plant reaction to the presence of the L-form of that pathogen. (Amijee et al. (1992); Biocontrol Science and Technology 2 203–214.

As has already been established in our European Patent a wide variety of associations have been achieved and we have found as yet, no restriction to this. Innumerable bacteria antagonistic to either or both bacterial and fungal plant pathogens are known to exist in nature and are important factors in the preservation of the ecological equilibria. Any of these can be selected for a desired antagonistic activity and thereafter its effect on the resistance of the plant may be determined. Our procedure offers therefore a wide range of possible options along with selection on the basis of desired activity, safety and ethical considerations.

According therefore to a first feature of the invention there is provided a process for protecting a host eukaryote or a part thereof, from attack by an invasive agent, which comprises; selecting a prokaryotic bacteria which is capable of forming an L-form association with said host, and introducing said bacterium into the said host; the invention being characterised in that said bacterium is also selected to be antagonistic to the invasive agent.

In a preferred embodiment of the invention the selected L-form bacterium is also selected to give resistance to the host against the entire forms of said bacterium. The introduction of the L-forms into the host eukaryote may be effected by:

1. injection of the host with a culture of an entire bacterium along with an effective amount of an L-form inducer and an osmoticum, or
2. by macerating eukaryotic host tissue which is infected with the L-form bacteria, and bringing the macerate or a filtrate thereof into contact with susceptible cells of the eukaryotic host;. or
3. by forming an osmotically compatible aqueous suspension of the L-form bacteria and bring the said suspension, or a filtrate thereof, into contact with susceptible cells of the eukaryotic host.

The host may be an angiosperm, a monocotyledonous or dicotyledonous plant. The invasive organisms may be prokaryotes or eukaryotes, for example, bacteria or fungi and may be pathogens or saprophytes.

This invention is useful for the protection of plants and their constituent parts including vegetative extensions and fruits, and thus provides, for example, an ecologically and ethically acceptable method of prolonging the shelf life of a soft fruit such as the strawberry or raspberry and vegetables such as Chinese cabbage and tomatoes. Further, some antagonistic bacteria such as, for example. *Pseudomonas antimicrobica* have a broad spectrum activity against both fungi and bacteria and hence protect host eukaryotes against undesired organisms. The invention thus seeks to provide a means of controlling disease both pre- and post-harvest so that the interest of the grower and crop utiliser can be achieved by the same protective treatment.

According therefore to the second aspect of the invention there is provided a eukaryotic plant or part thereof comprising L-form prokaryotic bacteria which bacteria are antagonistic to a selected invasive agent. The L-form prokaryotic bacteria may also protect the plant against entire forms of the bacteria selected. The plant may be a soft fruit such as the strawberry or raspberry, black current, red current or a vegetable such as Chinese cabbage, tomato, courgette, bean or potato. In one preferred opinion, when the soft fruit is a strawberry, the L-form bacteria may be *Pseudomonas antimicrobica*. Similarly *Pseudomonas antimicrobica* and *Erwinia herbicola* will protect the Chinese cabbage both during growth and against deterioration after harvest.

Figure 2:
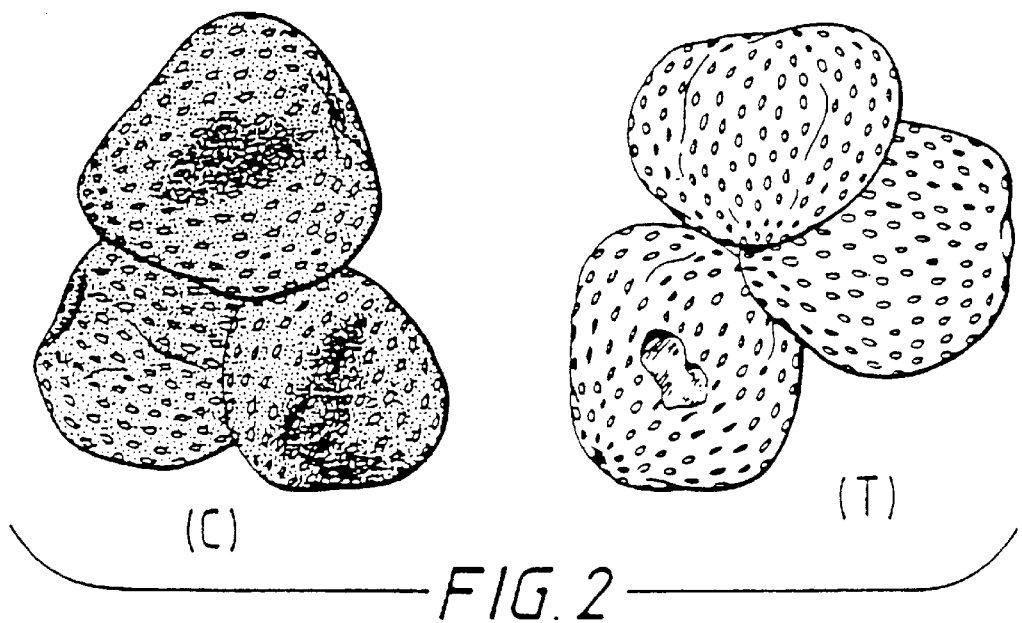

The invention will now be described, by way of illustration only, with reference to the following examples and in the accompanying graphic representatives of photographs In the Figures:

FIGS. 1 and 2 show a graphic representations of photographs showing strawberries stored for 23 days at 5° C., as discussed in Example 3.

The symbol (T) denotes results from Treated plans; and the symbol (C) denotes results from Control plants.

Figure 3:
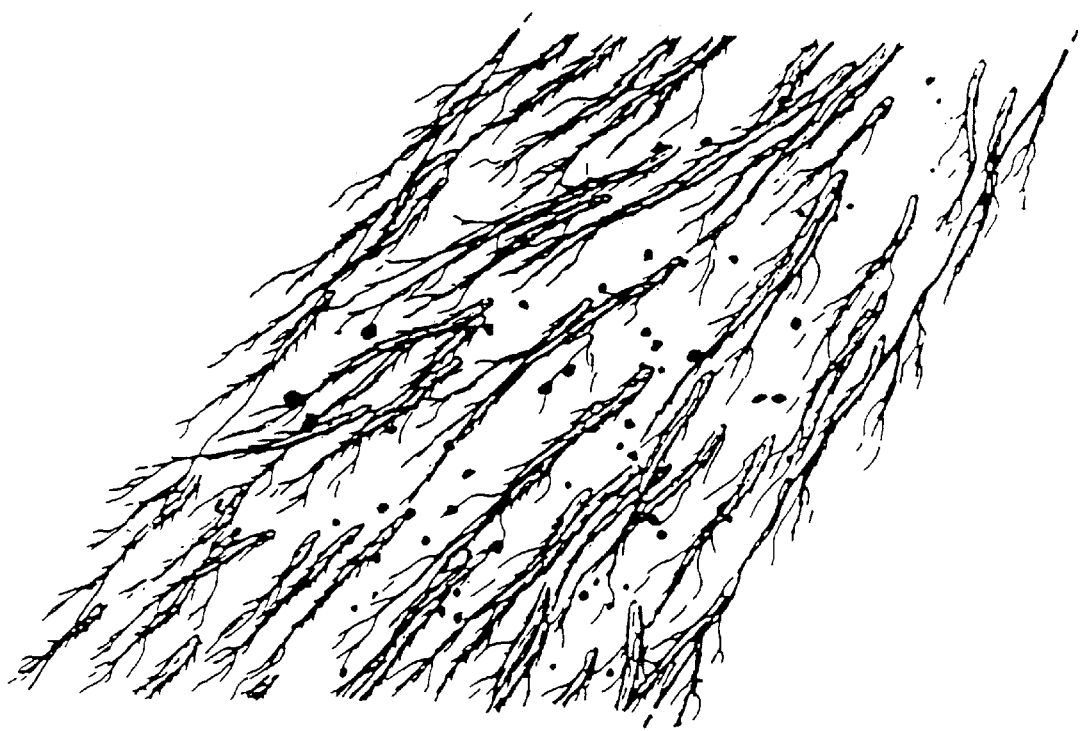
Figure 4:

FIGS. 3 and 4 show graphic representations of runner segments from strawberry plants stored for 7 days at ambient temperatures as discussed in Example 3.

The symbol (T) denotes results from Treated plants, and the symbol (C) denotes results from Control plants.

Figure 5:
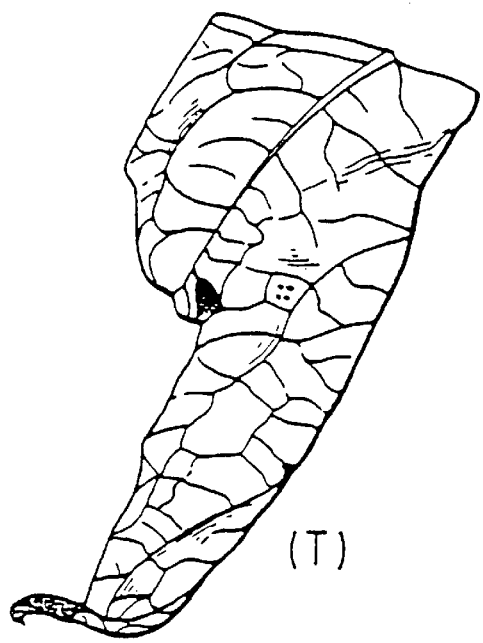
Figure 6:
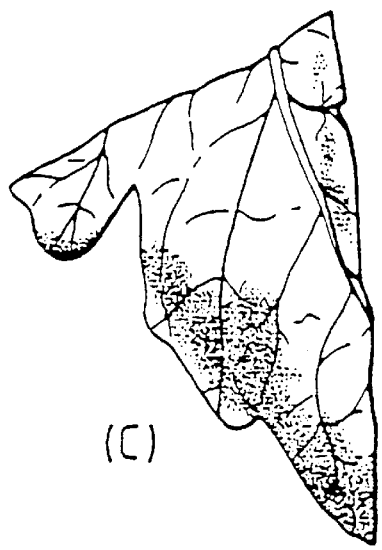

FIGS. 5 and 6 show graphic representations of photographs showing tomato leaflets stored at ambient temperatures for 10 days as discussed in Example 4.

The symbol (T) denotes results from Treated plants, and the symbol (C) denotes results from Control plants.

Figure 7:
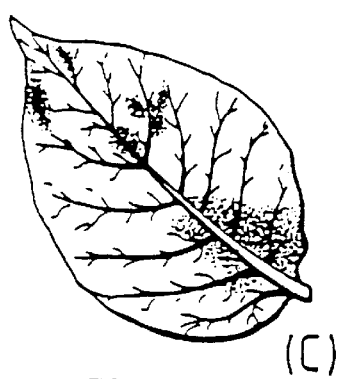
Figure 8:
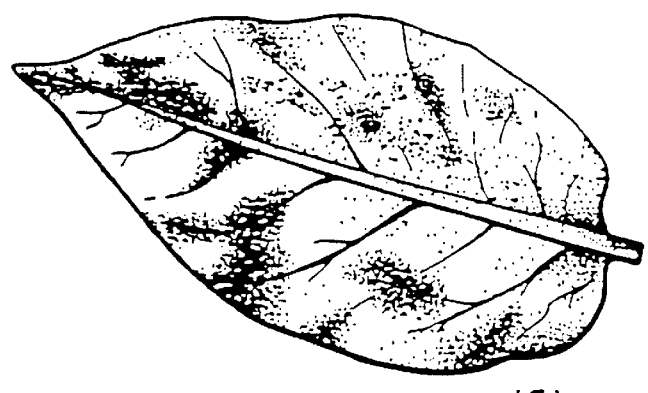

FIGS. 7 and 8 show graphic representations of photographs showing potato leaflets (unfrozen) stored for 5 days at ambient temperatures as discussed in Example 5.

The symbol (T) denotes results from Treated plants, and the symbol (C) denotes results from Control plants.

Figure 9:
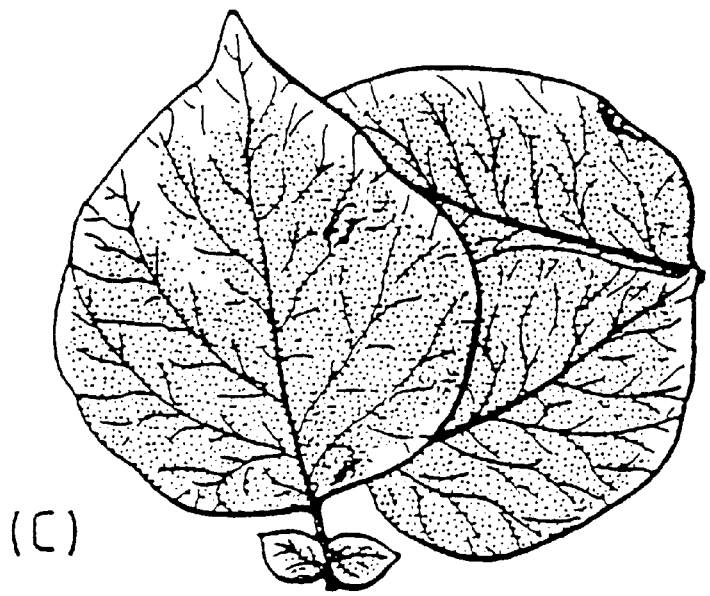
Figure 10:
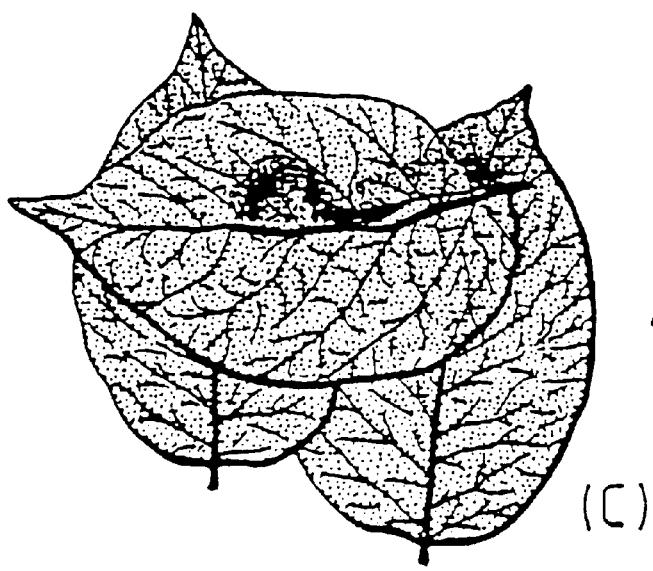

FIGS. 9 and 10 show graphic representations of photographs showing potato leaflets (frozen for 24 h @ −20° C.) and stored for 5 days at ambient temperatures as discussed in Example 5.

The symbol (T) denotes results from Treated plants, and the symbol (C) denotes results from Control plants.

Figure 11:
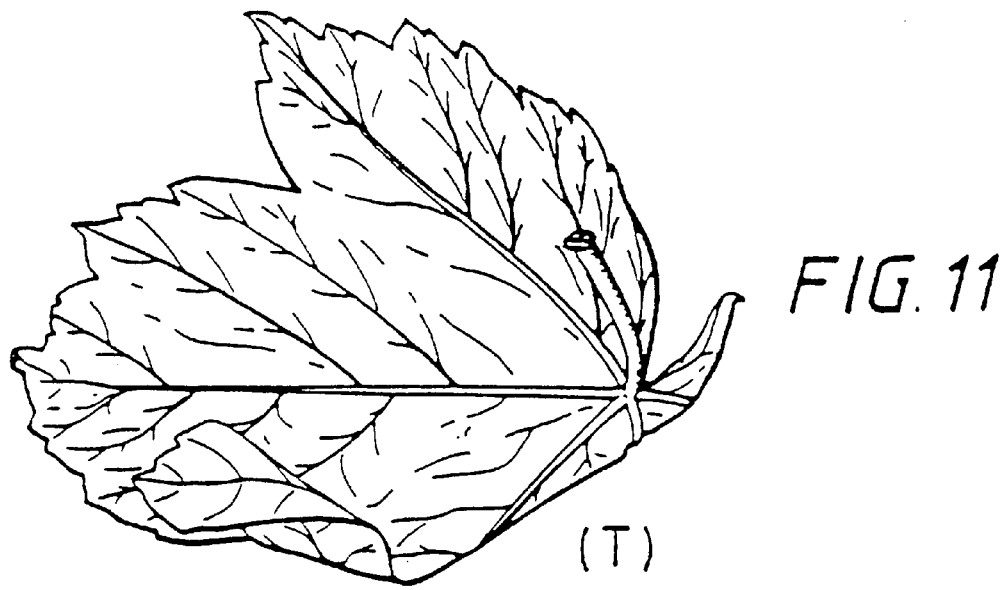
Figure 12:
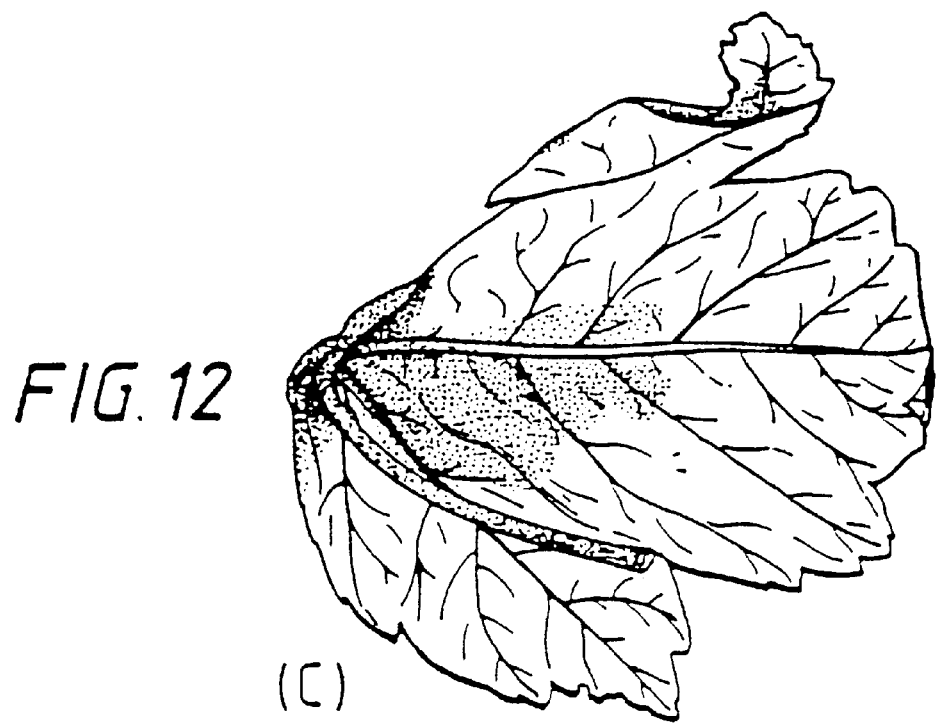

FIGS. 11 and 12 show graphic representations of photographs showing Sycamore leaflets as discussed in Example 6.

Figure 13:
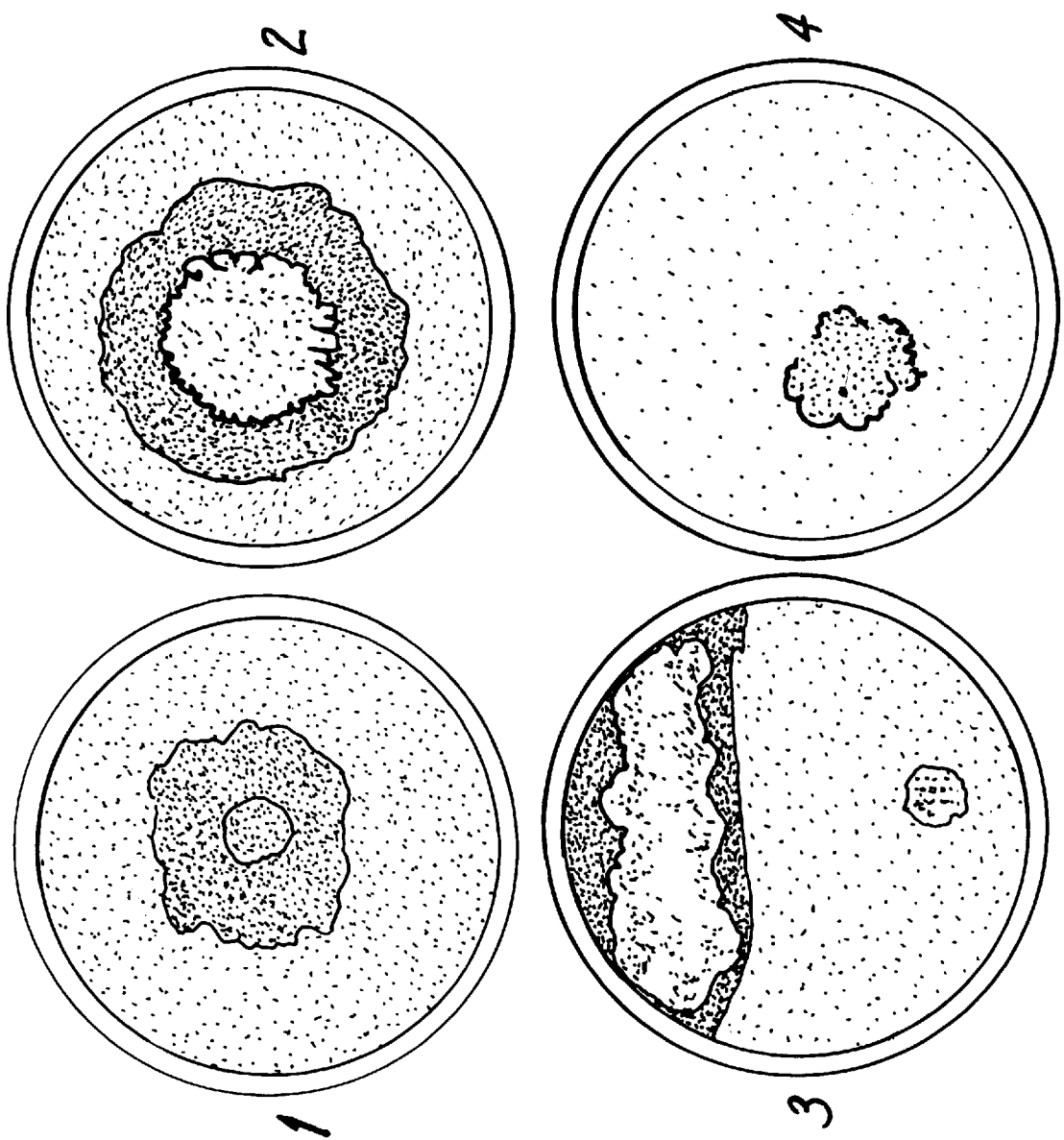

The symbol (T) denotes results from Treated plants, and the symbol (C) denotes results from Control plants; and FIG. 13 shows graphic representations of photographs showing the inhibitory effects of some bacterial isolates. Initial in vitro tests are discussed in Example 7.

These show:

1: *Ps. antimicrobica* inhibiting *Botrytis cinera,*

2: *B. subtilis* inhibiting Botrytis,

3: *Ps. antimicrobica* inhibiting Monilia spp; and

4: *Ps. fluorescens* inhibiting *Erw. carot v. atrosentica.*

EXAMPLE 1

Association of Chinese Cabbage (Brassica) with the L-form of *Pseudomonas antimicrobica* (NCIB 9898)

Preparation of L-form Inoculum:

The fresh growth from a glucose agar (g/l of water; peptone, 20; glucose, 10; sodium chloride, 5; agar, 15 at final pH 7.0) slope culture (18 h @ ambient temperature) of *Pseudomonas antimicrobica* was suspended to a slightly cloudy appearance of 20 ml of L-phase broth, consisting of (g/l of water); peptone, 5.0; sucrose, 200.0; glucose, 5.0; magnesium sulphate, 0.1 at final pH 7.0 which was sterilised by autoclaving prior to the addition (at 50° C.) of mycoplasma-screened, heat-inactivated horse serum (50 ml/l) and benzylpenicillin (5000 units/ml). The culture suspension was then subjected to mild rotary incubation for 24 h @ 30° C., after which it was deposited by centrifugation, resuspended under aseptic conditions in four 5 ml aliquots of fresh L-phase broth and varied as:

A. No addition.

B. Addition of 0.2 mg filter sterilised lysozyme/5 ml.

C. Addition of 60 μg filter sterilised phosphomycin/5 ml

D. No addition but heat-inactivated for 10 min. @ 80° C. to form control inoculum.

All variations were rotary incubated (100 rpm) for 24 h @ 30' in 50 ml Erlenmeyer flasks under aseptic conditions.

Preparation of Seedlings:

Washed Chinese cabbage seeds, previously surface-sterilised with alcohol and hypochlorite, were incubated on the surface of plates of water agar for 24 h @ ambient temperatures to achieve minimal visible emergence of radicles.

Inoculation of Seedlings:

Each germinated seed was inoculated with one drop of the appropriate inoculum (A to D) from a Pasteur pipette and incubation was continued in a plant growth cabinet at 25° C. for 24 h when 10 seedlings from each treatment were planted in trays of horticultural-grade compost. Growth was continued in the plant cabinet at 25° C.

Identification of Associations and Activity:

The seedlings were examined microscopically 24 h after inoculation. L-forms were observed in saline (0.85% aq) mounted root material by interference and phase contrast optics in the root hairs and root cortex cells of treatments A, B and C but not in treatment D (control).

At 4 weeks L-forms were similarly observed in the root cortex cells, while at 3 months plant sap extracts were found to be active in vitro (glucose agar plate/well method) against a susceptible test , pathogen, *Pseudomonas syringae pv phaseolicola*. This was in contradistinction to the sap from control plants which were inactive.

The presence in the plants of the L-forms of *Pseudomonas antimicrobica* had no deleterious effect on their health or growth.

Example 1 illustrates an ability to form a long-term association between a plant and the L-form of a saprophytic bacterium whereby the antagonism of the latter to a susceptible bacterial plant pathogen is expressed and perpetuated in the plant.

EXAMPLE 2

The Association of Chinese Cabbage (Brassica) with the L-form of *Erwinia herbicola* (Antagonistic Strain)

Preparation of L-form Inoculum:

The fresh growth of *Erwinia herbicola* from a 20 ml glucose agar slope culture (18 h @ 30° C.) was suspended and subcultured in 100 ml glucose broth (nutrients as for glucose agar) by rotary incubation (100 rpm) for 3 h @ 30° C. 10 ml of the subculture was applied by sterile pipette to the surface of a 50 ml slope of solid L-phase medium (as described in Example 1+agar 1%) to establish a two-phase (liquid/solid) culture environment. Incubation was continued for 18 h at ambient temperatures, at which time the liquid phase of the culture was available as an inoculum.

Seed Preparation:

Chinese cabbage seeds, previously surface sterilised by treatment with alcohol and hypochlorite, were incubated on the surface of water agar plates containing 1000 units/ml benzylpenicillin for 24 h @ ambient temperatures to achieve minimal visible emergence of the radicles. Each germinated seed was inoculated, using a Pasteur pipette, with one drop of the appropriate live or control (heat-inactivated for 10 min @ 80° C.) cultures. The developing seedlings were then planted into trays of horticultural grade compost and their growth continued under the same conditions for 10 days.

Plant Pathogen Challenge:

Both test and control plants were challenged by spraying the leaf surfaces with a fresh aqueous suspension (approximately 10 ** colony forming units/ml) of a virulent strain of the homologous plants pathogen, *Xanthomonas campestris*. The challenged plants were retained in a humid environment at 25° C. for a further 7 days.

Identification of Association and Activity:

Confirmation of L-form association was made by microscope examination of root cortex and petiole cells. The leaves of the test plants showed disease effects only where excess inoculum had inadvertently been applied. Such diseased areas remained defined and did not extend. The leaves of the control plants (treated with heat-inactivated culture) were extensively diseased with extending chlorosis and subsequent necrosis.

The presence of the L-form of *Erwinia herbicola* in the plants had no apparent deleterious effect on their health and growth.

Example 2 illustrates the long term association of Chinese cabbage with the L-form of an antagonistic bacterium unrelated to that used in Example 1. In this case, the protective activity was clearly demonstrated in vivo.

EXAMPLE 3

The Association of Cultivated Strawberry (Fragaria) with L-forms of *Pseudomonas antimicrobica*

Preparation of L-form Inoculum.

Fresh growth of *Pseudomonas antimicrobica* from a glucose agar (as previously defined) slope (24 h @ ambient temperatures) was used to form a faintly cloudy suspension in 20 ml L-phase broth containing 5000 units benzylpenicillin/ml and 0.1% disodium EDTA (ethylene diamine tetra-acetic acid).

The suspension was rotary incubated (100 rpm) for 24 h @ 30° C. 3.0 under aseptic conditions. The so-formed inoculum developed a marked pleomorphism with swollen rods attached to spheres and numerous L-form-like structures.

Treatment of Plants.

Four young strawberry plants (cv "Red Gauntlet") were planted in pots of peat compost. Two plants were subjected to live inoculum and two plants to the same but heat-inactivated (10 min @ 80° C.) inoculum. Each plant received approximately 0.5 ml inoculum, delivered by hypodermic needle into the developing crown tissue. The plants were grown under greenhouse conditions for 10 weeks until fruit was produced and ripened. No differences to the health and vigour of the plants were observed.

Identification of Activity:

On examination after 23 d storage at ~4° C. the berries from the treated plants were observed to have retained their original rich colour and healthy structured tissue. There was no evidence of deterioration and the few drops of expressed moisture in the base of the container were clear and apparently uncontaminated.

The berries from the control plants, also after 23 d storage in the same conditions, had turned a dominant brownish colour with a faint residual red still evident in a few parts of the surfaces. There was a marked development of moulds and the berries were decomposed. A copious brown opaque liquid had been expressed and had formed at the base of the container. This may be seen in FIGS. 1 and 2 where (T) indicates treated berries and (C) indicates a control.

Lengths of runner (approximately 5 cm) were removed from test and control plants 14 weeks after the inoculation process and frozen at −20° C. for 24 h. The runner segments were then placed on the surface of water agar (it aqueous agar) plates and retained at ambient temperatures for 7 d.

The runner segments removed from the treated plants showed no evidence of microbial development after 7 d at ambient temperatures. In contrast, the tissues from the control plants were heavily contaminated with fungal and bacterial growth. This may be seen in FIGS. 3 and 4 where (T) indicates treated vegetative tissue and (C) indicates control tissue. The treated tissue shows a very low bacterial colony formation whereas the control shows the establishment of significant bacterial colonisation.

Example 3 illustrates that the marked activity, ensuing from the association of the L-forms of *Ps. antimicrobica* with strawberry plants, extends to the fruit. It also indicates that the activity is sufficient to protect tissue which is vulnerable to storage depreciation. The protection of the runner tissue against microbial degradation is indicative of a systemic effect of the antagonism produced by the L-forms within the plant and suggests that the protective effect of the presence of the L-forms is passed to the daughter plants.

EXAMPLE 4

The Association of Tomato (Solanum) with L-forms of *Pseudomonas antimicrobica*

Preparation of L-form Inoculum.

Fresh growth of *Pseudomonas antimicrobica* from glucose agar (as previously defined) 18 h @ 30° C.) was used to form a faintly cloudy suspension in 5 ml glucose broth which was orbitally incubated (60 min @ 30° C. and 100 rpm) under aseptic conditions. 1 ml was transferred to a further 5 ml glucose broth and the short incubation repeated. The culture was then used to surface inoculate L-phase agar plates which were incubated at 25° C. for 18 h. The ensuing growth was harvested in saline (0.85% aq sodium chloride) to form the plant inoculum (the growth from one plate in 5 ml saline).

Treatment of Plants.

Tomato seeds (cv Alicante) were surface sterilised with alcohol and hypochlorite, washed in sterile water and germinated on water agar plates (4 d @ 25° C.) until radicle emergence was distinct. Using a Pasteur pipette each seedling (approximately 10 per plate) was drop inoculated with the live suspension or the same suspension heat-treated (10 min @ 80° C.). The inoculated seedlings were retained on the plates for 18 h and thereafter planted out in trays of commercial horticultural compost. When approximately 5 cm high, plants chosen at random were potted separately and grown on to maturity in greenhouse conditions.

Identification of Activity.

Both treated and control plants grew normally. After a growth period of 8 weeks, leaflets were excised from the plants placed in moist Petri dishes. The specimens were then held at ambient temperatures for 10d, when marked differences between the treated and control leaflets were evident. Those treated with L-forms showed only extended areas of chlorosis. This senescence was not accompanied by any other evidence of deterioration. The controls (from plants inoculated with heated inoculum) in contrast had uniformly changed colour to a dark brown accompanied by microbial deterioration. These results are shown in FIGS. 5 and 6.

Petiole sap expressed from leaves of treated and control plants were examined using the staphylococcal-antibody conjugate test. (This reagent was prepared according to the method against *Pseudomonas antimicrobica*). The positive agglutination reaction obtained with the sap of associated plants and the negative with the controls were considered to be supportive evidence of the presence of the L-forms. Example 4 illustrates a long term protective effect of an L-form association in a plant of a different Genus also producing a commercially viable fruit.

EXAMPLE 5

The Association of Potato Plants (Solanum) with the L-forms of *Pseudomonas antimicrobica*

Preparation of L-form Inoculum:

1 ml of an 18 h static culture of *Pseudomonas antimicrobica* in glucose broth (as previously described) was used to seed 5 ml of the same medium. This suspension was incubated for 1 h @ 30° C. on an orbital shaker (100 rpm) under aseptic conditions. The bacterial cells were deposited by centrifugation (15 min @ 3000 rpm). The cells were re-suspended in 5 ml glucose broth and further cultivated at 30° C. on an orbital shaker (100 rpm) for 1 h. The culture was then surface plated using an inoculating wire loop on L-phase agar (see Examples 1 and 2) and incubated for 18 h @ 25° C. A cloudy suspension of this growth in isotonic saline (0.85% sodium chloride) was used as the inoculum.

Treatment of Plants:

Potato tubers (cv Morene) were inoculated by fine hypodermic needle into the base tissues of all developing "eyes" (approximately 1.0 ml/site). Other tubers were similarly inoculated with the heat-inactivated suspension (10 min @ 80° C.). The tubers were planted separately in large pots of horticultural grade compost and retained under greenhouse conditions for 6 weeks. All plants grew normally, producing healthy tubers.

Identification of Association and Activity:

The sap expressed from the petioles of treated plants showed a weak positive reaction masked by a degree of autoa-gglutination when tested by the staphylococcal-antibody conjugate reagent (ref. Example 4). Leaflets were excised from both treated and control plants and placed in moist conditions in Petri dishes. The leaflet surfaces were dusted with the conidia of *Botrytis cineria* and left at ambient temperature for 5 d with and without a period of freezing of 24 h @ −20° C. The freezing procedure ensured that the plant cell contents (including the antagonistic L-form metabolites, if present) were released. The unfrozen leaflets showed a distinct different between the treated and control plants. The treated material was partly chlorotic but rigid and otherwise healthy and visibly uncontaminated. The control leaflets were uniformly dark brown, limpid and partly decomposed. The leaflets which had been initially frozen also showed marked differences. The treated tissues were dark green but showed no visible evidence of microbial growth in contrast with the controls which were dark brown and markedly decomposed with extensive surface mould broth. These results are shown in FIGS. 7, 8, 9 and 10.

Example 5 illustrates the ability to produce L-form associations in tubers which can give rise to an extended association and an antagonistic effect on degradative microbial activity in the subsequent vegetative growth.

EXAMPLE 6

The Association of an Antagonistic Strain of *Pseudomonas fluorescens* L-forms with Sycamore (Acer)

Preparation of L-form Inoculum.

A saprophytic, antagonistic strain of *Pseudomonas fluorescens*, originally isolated from raspberry (Rubus) flowers, was cultured for 24 h on glucose agar. A faintly cloudy suspension of this fresh growth in saline (0.85% sodium chloride) was inoculated as single, discrete drops from a Pasteur pipette on the surface of L-phase agar containing 5000 units benzyl penicillin/ml. The growth appearing on the plates after an incubation of 18 h @ 25° C. was suspended in saline (1 plate/5 m) to constitute the inoculum. Phase contrast microscopy of this suspension showed a high proportion of L-form-like cells with some pleomorphic rods.

Treatment of Plants.

Young sycamore trees (2 years) were removed from their natural siting and potted in large containers with a mixture (1:1) of horticultural compost and garden soil. Inoculation was carried out at a dormant stage (late winter). The suspensions (live and heat inactivated for 10 min @ 80° C.) were inoculated into the stem cambial tissue by hypodermic to a level of saturation. The wound was thereafter protected from drying for 24 h with adhesive tape.

Recognition of Activity.

Both the treated and control plants developed normally in outside conditions during the spring period without visible distinction. After a period of growth of 6 weeks following leaf appearance leaves were removed, inoculated with conidia of *Botrytis cineria* and placed in damp Petri dishes at indoor ambient temperatures. After a period of 3 weeks, during which no deterioration was obvious, a mixed fungal colonisation appeared, rapidly developed and destroyed the affected leaf and petiole tissues of the control plants. During the same period, the treated tissues showed no evidence of deterioration. (See FIGS. 11 and 12).

EXAMPLE 7

The Primary Selection of Antagonistic Bacteria for Protective Association as L-forms in Plants Dilute suspensions of crude material from fresh plants and soil samples taken at random, were streak-plated with a wire inoculating loop on the surface of sterile glucose agar plates which were incubated for 2 d to 7 d @ 25° C. The different bacterial colonies which subsequently appeared were spot inoculated on fresh plates of the same glucose agar (approximately 6 inoculations distributed over the surface of each plate). After an initial incubation of 24 h @ 25° C., the surface of the plates were inoculated with the conidia from a fructifying culture of a test fungus (e.g., *Botrytis cineria*). The conidia were evenly distributed by "tapping" an inverted Petri dish containing the fungus over the agar surface supporting the bacterial growths. The inoculated plates were then incubated for up to 7 d @ 25° C. and examined for zones of inhibition affecting the development of the test fungus. Bacteria colonies demonstrating such activity were selected for purification checks and confirmation of the antagonism.

Isolations were also made from glucose agar plates which had been exposed freely to air for periods of up to 3 h. The random contaminating bacterial colonies were subjected to the same tests as indicated above. The most active bacteria isolated (as judged by the arbitrary in vitro tests) were induced to an L-form state and associated with Chinese cabbage seedlings for an essential in vivo assessment.

FIG. 13 shows examples of in vitro inhibitory effects on pathogenic fungi and a bacterium likely to be useful in plant associations.

EXAMPLE 8

The Use of Antisera for the Detection of Slant Association with *Ps. antimicrobica*

Antisera were produced in 2 rabbits after a series of immunising inoculations using a preparation (cell membrane fraction) derived from a pure culture of *Ps. antimicrobica*. The nature of the inoculant was chosen to provide an "antigen" closely related to L-forms, i.e., without cell-wall constituents.

The antisera proved to have a satisfactory specificity for *Ps. antimicrobica*, there being no agglutinating reaction with other pseudomonades tested.

The slide agglutinating reactions of the antisera at dilutions of 1:1 and 1:10 with equal volumes of a saline suspension of *Ps. antimicrobica* were strong.

Stained micrococcus conjugates with the antisera were prepared according to the method of Lyons & Taylor (1990). Slide tests were carried out using freshly homogenised conjugates.

The following results were obtained:

| "ANTIGEN" | "AGGLUTINATION" |
| --- | --- |
| Ps. antimicrobica | ++ |
| Ps. fluorsescens | – |
| Ps. syringae pv phaseolicola | – |
| Erw. herbicola | – |
| Strawberry (petiole) untreated | ++ auto-agglutination |
| Strawberry (petiole) treated | ++ auto-agglutination |
| Strawberry (leaf) untreated | ++ auto-agglutination |
| Strawberry (fruit) (untreated) | ++ auto-agglutination |
| Tomato (leaflet) untreated | +/– auto-agglutination |
| Tomato (fruit) untreated) | +/– auto-agglutination |
| Tomato (leaflet) treated | + auto-agglutination (valid) |
| Potato (leaflet) untreated | +/– auto-agglutination |
| Potato (leaflet) treated | + auto-agglutination (valid) |
| Chinese cabbage (leaf) untreated | – |
| Chinese cabbage (leaf) treated | + (valid) |

Note: The designation ++ auto-agglutination indicates that the results are invalid in this case.

The tissue extracts from strawberry cultivars; Redgauntlet, Elsanta, Tamella, Sweetheart and wild strawberry all strongly auto-agglutinated the rabbit anti-*Ps.am* sera/conjugates, rendering the latter useless for L-form detection in the plant, but the results were valid for the Tomato, Potato and Chinese cabbage.

What is claimed is:

1. A process for protecting a part or all of a host eukaryotic plant from attack by an invasive agent, the process comprising:
   obtaining a prokaryotic bacterium selected from the group consisting essentially of *Pseudomonas antimicrobica, Pseudomonas fluorescens* or *Erwinia herbicola* that is capable of forming an in vivo L-form association with a host eukaryotic plant;
   inducing the prokaryotic bacterium to form an L-form of the prokaryotic bacterium; and
   introducing the L-form of the prokaryotic bacterium into the part or all of a host eukaryotic plant to form a protected part or all of a host eukaryotic plant, wherein the part or all of the host eukaryotic plant is selected from the group consisting essentially of a strawberry, a raspberry, a black currant, a red currant, a tomato, a Chinese cabbage, a courgette, a new potato, a sycamore, or any combination thereof, and wherein the protected part or all of the host eukaryotic plant is antagonistic to the invasive agent in vivo.

2. The process according to claim 1 wherein the protected part or all of the host eukaryotic plant resists attack by the prokaryotic bacterium.

3. The process according to claim 1 wherein introducing the L-form of the prokaryotic bacterium into the part or all of the host eukaryotic plant comprises:
   injecting the part or all of the host eukaryotic plant with the prokaryotic bacterium, an amount of an L-form inducer and an osmoticum that are effective to form the L-form of the prokaryotic bacterium.

4. The process according to claim 1 wherein introducing the L-form of the prokaryotic bacterium into the part or all of the host eukaryotic plant comprises:
   macerating a host eukaryotic plant tissue comprising the L-form of the prokaryotic bacterium to form a macerate or a filtrate;
   contacting the part or all of the host eukaryotic plant with the macerate or the filtrate.

5. The process according to claim 1 wherein introducing the L-form of the prokaryotic bacterium into the part or all of the host eukaryotic plant comprises:
   forming an aqueous suspension of the L-form of the prokaryotic bacterium; and
   contacting the aqueous suspension or a filtrate thereof with the part or all of the host eukaryotic plant.

6. The process according to claim 1 wherein the invasive agent is not the prokaryotic bacterium.

7. The process of claim 1 wherein the protected part or all of the host eukaryotic plant resists attack by the invasive agent.

8. The process of claim 1 wherein the protected part or all of the host eukaryotic plant resists disease, deterioration, chlorosis, necrosis, senescence, decomposition, or any combination of any of these caused by the invasive agent.

9. A protected part or all of a host eukaryotic plant prepared by the process of claim 1, the protected part or all of the host eukaryotic plant comprising:
   a part or all of a host eukaryotic plant that is selected from the group consisting essentially of a strawberry, a raspberry, a black currant, a red currant, a tomato, a Chinese cabbage, a courgette, a new potato, a sycamore, or any combination thereof and an L-form of a prokaryotic bacterium selected from the group consisting essentially of *Pseudomonas antimicrobica, Pseudomonas fluorescens* or *Erwinia herbicola*, wherein the L-form of the prokaryotic bacterium is associated in the part or all of the host eukaryotic plant to form the protected part or all of the host eukaryotic plant, and wherein the protected part or all of the host eukaryotic plant is antagonistic to an invasive agent in vivo.

10. A process for protecting a part or all of a host eukaryotic plant from attack by an invasive agent, the process comprising:
    selecting a prokaryotic bacterium from the group consisting essentially of *Pseudomonas antimicrobica, Pseudomonas fluorescens* or *Erwinia herbicola* that is capable of forming an in vivo L-form association with a host eukaryotic plant;
    inducing the prokaryotic bacterium to form an L-form of the prokaryotic bacterium, wherein the prokarvotic bacterium is antagonistic to an invasive agent; and
    introducing the L-form of the prokaryotic bacterium into the part or all of the host eukaryotic plant, wherein the part or all of the host eukaryotic plant is selected from the group consisting essentially of a strawberry, a raspberry, a black currant, a red currant, a tomato, a Chinese cabbage, a courgette, a new potato, a sycamore, or any combination thereof to form a protected part or all of the host eukaryotic plant, wherein the protected part or all of the host eukaryotic plant resists attack by the invasive agent in vivo.

11. The process of claim 10 wherein the protected part or all of a host eukaryotic plant comprises:

the L-form of the prokaryotic bacterium, wherein the L-form of the prokaryotic bacterium is associated in the part or all of the host eukaryotic plant to form the protected part or all of the host eukaryotic plant, wherein the prokaryotic bacterium is antagonistic to an invasive agent, and wherein the protected part or all of the host eukaryotic plant resists attack by the invasive agent in vivo.

12. A process for protecting a part or all of a host eukaryotic plant from attack by an invasive agent, the process comprising:

selecting a prokaryotic bacterium from the group consisting essentially of *Pseudomonas antimicrobica, Pseudomonas fluorescens* or *Erwinia herbicola* that is capable of forming an in vivo L-form association with a host eukaryotic plant;

inducing the prokaryotic bacterium to form an L-form of the prokaryotic bacterium; and introducing the L-form of the prokaryotic bacterium into the part or all of the host eukaryotic plant to form the protected part or all of the host eukaryotic plant, wherein the protected part or all of the host eukaryotic plant is selected from the group consisting essentially of a strawberry, a raspberry, a black currant, a red currant, a tomato, a Chinese cabbage, a courgette, a new potato, a sycamore, or any combination thereof, and wherein the host eukaryotic plant resists attack by the invasive agent in vivo.

13. The process of claim 12 wherein the protected part or all of a host eukaryotic plant comprises:

the L-form of the prokaryotic bacterium, wherein the L-form of the prokaryotic bacterium is associated in the part or all of the host eukaryotic plant to form the protected part or all of the host eukaryotic plant, and wherein the protected part or all of the host eukaryotic plant resists attack by an invasive agent in vivo.

* * * * *